United States Patent [19]

Hofer

[11] Patent Number: 5,047,717

[45] Date of Patent: Sep. 10, 1991

[54] METHOD AND APPARATUS FOR MEASURING INTERNAL MECHANICAL STRESS OF A FERROMAGNETIC BODY BY DETERMINING THE THIRD HARMONIC OF THE INDUCTION

[75] Inventor: Gerhard Hofer, Röttenbach, Fed. Rep. of Germany

[73] Assignee: Siemens Aktiengesellachaft, Munich, Fed. Rep. of Germany

[21] Appl. No.: 446,469

[22] Filed: Dec. 4, 1989

[30] Foreign Application Priority Data

Dec. 7, 1988 [EP] European Pat. Off. ...... 88 120 460.6

[51] Int. Cl.$^5$ .................... G01B 7/24; G01R 33/18
[52] U.S. Cl. ..................................... 324/209; 73/779
[58] Field of Search ................... 324/209; 73/763, 779

[56] References Cited

U.S. PATENT DOCUMENTS 3,535,625  10/1970  Pratt .
3,636,437  1/1977   Souland Jr. et al. .
3,798,537  3/1974   Dahm ............................... 324/209

OTHER PUBLICATIONS

U.S. Publication "Reviews of Modern Physics" vol. 21, No. 4, Oct. 1949, article Physical Theory of Ferromagnetic Domains by Kittel, pp. 541–583.

Primary Examiner—Walter E. Snow
Attorney, Agent, or Firm—Herbert L. Lerner; Laurence A. Greenberg

[57] ABSTRACT

A method and apparatus for measuring the mechanical internal stress of a body of ferromagnetic material includes generating a sinusoidal magnetic field at given site of a ferromagnetic body. First and second amplitudes of the third harmonic component of the induction at first and second measuring sites at the body being mutually spaced apart by an angle of 90° with respect to the given site, are measured. An associated first curve from a first predetermined family of curves representing the third harmonic component of the induction as a function of the mechanical stress for the first amplitude, is located. An associatead second curve from a second predetermined family of curves representing the third harmonic component of the induction as a function of the mechanical stress for the second amplitude, is located. Especially the first family of curves is associated with a first predetermined measuring direction or a direction parallel thereto and the second family of curves is associated with a second measuring direction perpendicular to the first predetermined measuring direction. A point of intersection of the first and the second curves is determined. A given direction is defined by a connecting line passing through the given site of the sinusoidal magnetic field and through the first measuring site. The abscissa value of the point of intersection beginning at a predetermined abscissa value is determined as a measured value for the magnitude of the mechanical internal stress in the given direction.

6 Claims, 3 Drawing Sheets

METHOD AND APPARATUS FOR MEASURING INTERNAL MECHANICAL STRESS OF A FERROMAGNETIC BODY BY DETERMINING THE THIRD HARMONIC OF THE INDUCTION

The invention relates to a method and an apparatus for measuring the internal mechanical stress or strain of a body made of ferromagnetic material. It relates in particular to non-destructive testing of turbine blades.

Ferromagnetic materials are used, for instance, to construct turbine blades. Other ferromagnetic parts are also used in industry. In order to provide early detection of flaws in the material structure of such structural parts, the location and measurement of internal mechanical stresses of the ferromagnetic part are performed in the field of materials testing.

Many previously known methods for locating and measuring the internal stresses of a ferromagnetic body or part entail destruction of a sample of the body or part. Such methods are therefore not very suitable for regular checking of the parts. Moreover, they are usually labor-intensive. Besides that method, non-destructive methods for measuring internal mechanical stresses are available. In such methods, the part involved is tested by ultrasound or X-rays, for instance. In both kinds of methods, high measurement accuracy is sought. Another method of non-destructive measurement of internal stresses makes use of acoustical Barkhausen noise (W. A. Theiner and P. Holler, Magnetische Verfahren zur Spannungsermittlung [Magnetic Methods of Stress Detection], HTM Appendix entitled "Eigenspannungen und Lastspannungen" [Internal Stresses and Load Stresses], Carl Hauser Verlag, Munich 1982, pp. 156–163).

It is known in principle (C. Kittel, Physical Theory of Ferromagnetic Domains, Rev. Mod. Phys. 21, 1949, page 541) that the magnetic properties of a ferromagnetic material, such as hysteresis, are affected by mechanical stresses induced by magnetoelastic interaction.

For example, if a sinusoidal magnetic field acts upon a ferromagnetic material, the resultant magnetic induction is not precisely sinusoidal but instead is distorted by comparison. One reason for the distortion is the magnetic hysteresis and non-linear permeability of the material. The distorted induction includes harmonic components, which are dependent on the hysteresis.

Experimental tests of the dependency of the third harmonic component of the magnetic induction that is created when a sinusoidal exciter field acts upon a material, specifically the dependency on the mechanical stress applied and on the state of the material, are also known (H. Kwun, G. L. Burkhardt, Nondestructive Measurement of Stress in Ferromagnetic Steels using Harmonic Analysis of Induced Voltage, NDT International, Vol. 20, No. 3, June 1987). In those tests, it was demonstrated that in a material which is free of internal stress, the third harmonic amplitude, which is measured parallel to the load stress field, increases with an increasing load stress field. In contrast, the third harmonic amplitude measured vertically or perpendicularly to the load stress field decreases with increasing load stress. In that case, the point of intersection of the two thus-ascertained load/amplitude curves is at zero. A tensile internal stress present in the material shifts the point of intersection toward the left, while a compressive internal stress shifts the point of intersection toward the right.

The invention is based on the concept that the dependency of a harmonic component of the magnetic induction, in particular the third harmonic component, on the applied mechanical stress can be utilized for non-destructive measurement of mechanical stresses, in particular internal stresses. What must be taken into account is that the harmonic component is affected not only by the applied stress but also by the state of the material.

It is accordingly an object of the invention to provide a method and apparatus for measuring the internal mechanical stresses in a ferromagnetic body, which overcomes the hereinafore-mentioned disadvantages of the heretofore-known methods and devices of this general type, which works non-destructively and without contact, and which makes it possible to determine with high accuracy both the quantity of an arbitrary component of the mechanical internal stress in the material and its direction.

With the foregoing and other objects in view there is provided, in accordance with the invention, a method for measuring the mechanical internal stress of a body of ferromagnetic material, which comprises generating a sinusoidal magnetic field at given site of a ferromagnetic body; measuring first and second amplitudes of the third harmonic component of the induction at first and second measuring sites at the body being mutually spaced apart by an angle of 90° with respect to the given site; locating an associated first curve from a first predetermined family of curves representing the third harmonic component of the induction as a function of the mechanical stress for the first amplitude, and locating an associated second curve from a second predetermined family of curves representing the third harmonic component of the induction as a function of the mechanical stress for the second amplitude, associating especially the first family of curves with a first predetermined measuring direction or a direction parallel thereto and associating the second family of curves with a second measuring direction perpendicular to the first predetermined measuring direction; determining a point of intersection of the first and the second curves; and defining a given direction by a connecting line passing through the given site of the sinusoidal magnetic field and through the first measuring site, and determining the abscissa value of the point of intersection beginning at a predetermined abscissa value as a measured value for the magnitude of the mechanical internal stress in the given direction.

The selection of the first measuring site depends on the internal stress component to be ascertained in the body being tested. In parts that have a particular shape and particular dimensions, all that is often necessary is to measure the internal stress component in a certain direction, for instance in the direction of the greatest length of the part.

In a common coordinate system of two families of calibration curves, the amplitude values which are measured are plotted on the ordinate as a first and second ordinate value. The families of calibration curves indicate the course of the amplitudes of the third harmonic components of the magnetic inductions in a sample of the material as a function of known mechanical stresses to be imposed from outside. The first family of calibration curves indicates the course of the amplitude measured parallel to the applied mechanical stress. The second calibration curve indicates the course of the amplitude vertically of or perpendicularly to the applied mechanical stress. In order to determine the quantity of the internal mechanical stress, a calibration curve of the first family passing through the first ordinate value, and a calibration curve of the second family passing through the second ordinate value are selected. Then the abscissa value of the point of intersection of these two calibration curves is recorded as the quantity of the internal mechanical stress.

The magnetic properties of a ferromagnetic material, such as hysteresis, are affected by mechanical stresses, because of magnetoelastic linkages. For instance, if a sinusoidal magnetic field is applied to ferromagnetic material, the resultant magnetic induction is not sinusoidal but rather distorted. The reasons for the distortion are the magnetic hysteresis and the permeability of the material, which is not linear. However, the distorted wave of the resultant magnetic induction includes harmonic components dependent on the hysteresis.

It has already been ascertained that the third of the harmonic components of the resultant magnetic induction depends on the mechanical stress of a ferromagnetic part being tested. The amplitude of the third harmonic component, measured at a site remote from the site of generation of the sinusoidal magnetic field in the direction of the mechanical stress, increases with increasing stress. The amplitude of the third harmonic component of the magnetic induction, measured at a site that is vertically or perpendicularly remote from the direction of the mechanical stress, decreases with increasing stress. The two functions therefore have a point at which they intersect.

In a coordinate system in which the mechanical stress is plotted on the abscissa and the amplitude of the third harmonic component of the measured induction is plotted on the ordinate, the intersection has the abscissa value of zero, unless the material of the part has an internal mechanical stress. However, if it does have an internal mechanical stress, then the aforementioned point of intersection shifts in the direction of the abscissa. According to the invention, this effect is used for measuring internal mechanical stresses in ferromagnetic material.

If there is no internal mechanical stress, then the amplitude of the third harmonic component of the magnetic induction is of equal magnitude at both measuring sites and is located at the abscissa value of zero.

However, if there is an internal mechanical stress, then for the two measuring sites, the values of the amplitudes of the third harmonic component of the magnetic induction at the abscissa value of zero differ from one another, in the absence of external stresses. For the abscissa value of zero, two different ordinate values result.

In order to determine the quantity of the internal mechanical stress, the two amplitude values of the third harmonic components of the induction for a selected stress direction and for the direction vertically or perpendicularly thereto, are used.

First, however, families of calibration curves are required, which are defined beforehand for the structural part made of the ferromagnetic material to be tested. To this end, for the part to be tested, the course of the amplitude of the third harmonic component of the magnetic induction is determined as a first family of calibration curves at a site that is remote from the site of generation of the sinusoidal magnetic field in the direction of the external stress, as a function of known external mechanical stresses that act upon the part. As a second family of calibration curves, the course of the amplitude is determined at a site that is vertically or perpendicularly remote from the direction of the external stress. These calibration measurements are performed in a portion of material that is free of internal stresses.

The two families of calibration curves are plotted in a coordinate system as described above.

Next, the two amplitude values measured for the third harmonic components of the induction are plotted on the ordinate of the coordinate system of the calibration curves. The ordinate value for the amplitude in the stress direction which is selected defines a curve from the first family of curves. The ordinate value for the amplitude perpendicular to the selected stress direction defines a curve from the second family of curves. The two curves through the ordinate values form an intersection. The abscissa value of this intersection in the coordinate system of the families of calibration curves is equivalent to the quantity of the internal mechanical stress. If the magnitude of the internal mechanical stress is negative, a compressive internal stress is present; if it is positive, a tensile internal stress is present.

An advantage of the method according to the invention is that the quantity and magnitude of components of internal mechanical stresses in ferromagnetic material can be determined unequivocally, after a series of calibration measurements is performed.

In accordance with another mode of the invention, there is provided a method which comprises precisely determining the direction of the primary internal mechanical stress in a body of ferromagnetic material, by varying or rotating the measurement sites, for instance, relative to the site of generation of the sinusoidal magnetic field, while maintaining the angular spacing of 90°, until a maximum for the third harmonic component of the magnetic induction is recorded at one of the measuring sites and a minimum is recorded at the other. The direction determined by the site of generation of the sinusoidal magnetic field and by the site of the maximum, is recorded as the direction of the internal mechanical stress.

In accordance with an added mode of the invention, there is provided a method which comprises generating the sinusoidal magnetic field with an exciter coil, for instance.

In accordance with an additional mode of the invention, there is provided a method which comprises measuring the induction stresses with measuring coils, for instance, in order to determine the magnetic inductions.

With the objects of the invention in view, there is also provided an apparatus for measuring the internal mechanical stress of a body of ferromagnetic material, comprising an exciter coil for generating a magnetic induction with a third harmonic component, the exciter coil being movable toward a body to be tested and having an axis, two measuring coils being associated with the exciter coil and being spaced apart by an angle of 90° from the axis of the exciter coil, the measuring coils having axes aligned parallel to the axis of the exciter coil, filters connected to the measuring coils for passing only the third harmonic component of the magnetic induction, an evaluation logic connected to the filters, and a display unit connected to the evaluation logic.

The measuring coils are rotatable about the longitudinal axis of the exciter coil, for instance, while maintaining the same angular spacing. The evaluation logic may be a computer.

In accordance with a concomitant feature of the invention, there is provided a positioning unit connected to the measuring coils, the exciter coil, and the display unit, in order to control a motion of the measuring coils and to suitably display it.

The method for measuring internal mechanical stresses of a part made of ferromagnetic material can be performed quickly and reliably, with the apparatus according to the invention described above.

In particular, the invention affords the advantage of only requiring measurements of induction stresses that can be performed by simple means, in order to determine both the magnitude and the direction of internal mechanical stresses in parts made of ferromagnetic material, using calibration curves that are simple to prepare.

Other features which are considered as characteristic for the invention are set forth in the appended claims.

Although the invention is illustrated and described herein as embodied in a method and apparatus for measuring internal mechanical stress or strain of a ferromagnetic body, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIGS. 3-6 are graphs with coordinate systems showing the amplitude of the third harmonic component of the magnetic induction as a function of the mechanical stress, wherein FIG. 3 shows families of calibration curves;

FIG. 4 shows measured values in a state which is free of internal stresses;

FIG. 5 shows measured values with tensile internal stress; and

Figure 6:
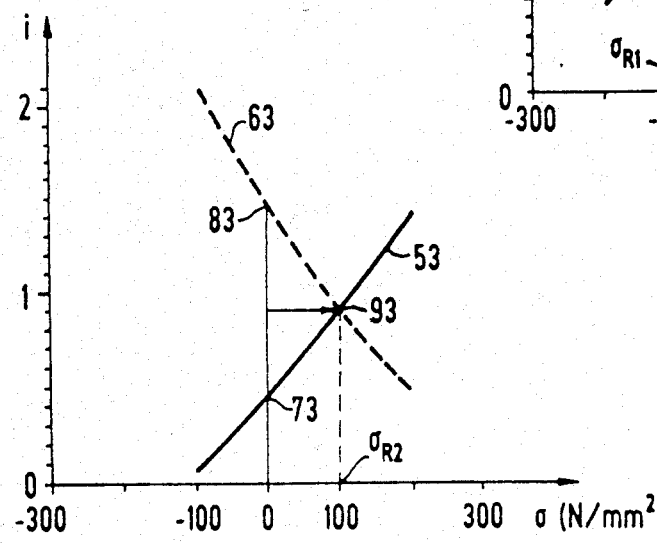

FIG. 6 snows measured values with compressive internal stress.

Figure 1:
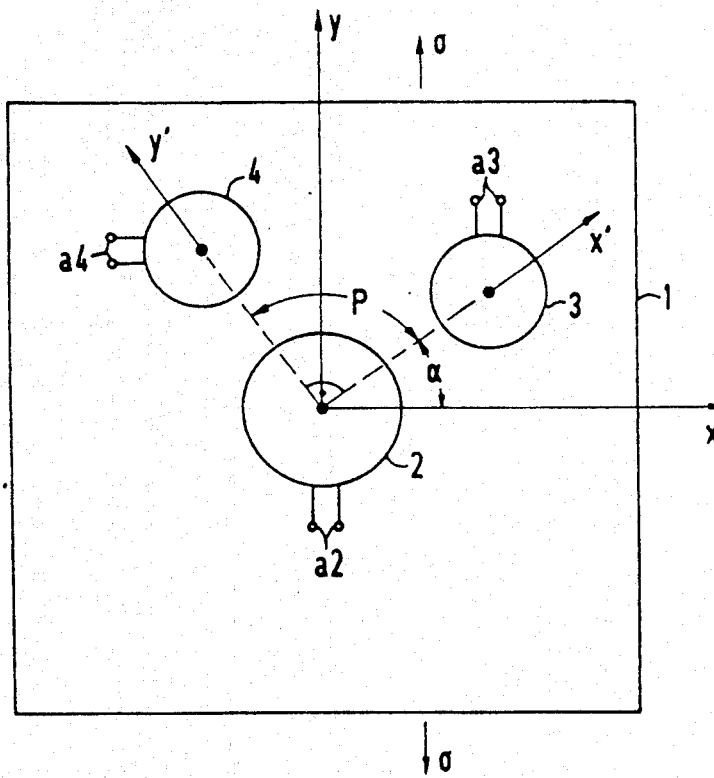
FIG. 1 is a diagrammatic, top-plan view of the basic structure of an apparatus for measuring internal mechanical stresses in a ferromagnetic body on which the apparatus is disposed.

Referring now to the figures of the drawing in detail and first, particularly, to FIG. 1 thereof, there is seen a test head of an apparatus for determining the internal mechanical stresses or strains in a ferromagnetic body 1, for instance a turbine blade. An exciter coil 2 of the apparatus is disposed at the origin of a coordinate system x, y, where x and y are intended to represent defined directions in the body 1. A voltage a2 is applied to the exciter coil 2. Two measuring coils 3 and 4, are spaced apart by an angle of 90° from the axis of the exciter coil 2, are oriented parallel to the exciter coil 2 and are as close as possible to the exciter coil 2 and the body 1. The measuring coils 3 and 4 are located on respective axes x', y', which form an angle $\alpha$ with the axes x, y. The measuring coils 3 and 4 are movable in common about and relative to the exciter coil 2, while maintaining the angular spacing of 90°. This is represented by a double arrow P. The exciter coil 2 is subjected to a sinusoidal alternating voltage, creating a sinusoidal magnetic field in the ferromagnetic body 1. The region of homogenous excitation extends as far as the region of the measuring coils 3 and 4. Measurement signals a3 and a4 originate at the measuring coils 3 and 4.

The unit formed of the coils 2, 3, 4 is preferably displaceable in the x and/or y direction.

Figure 2:
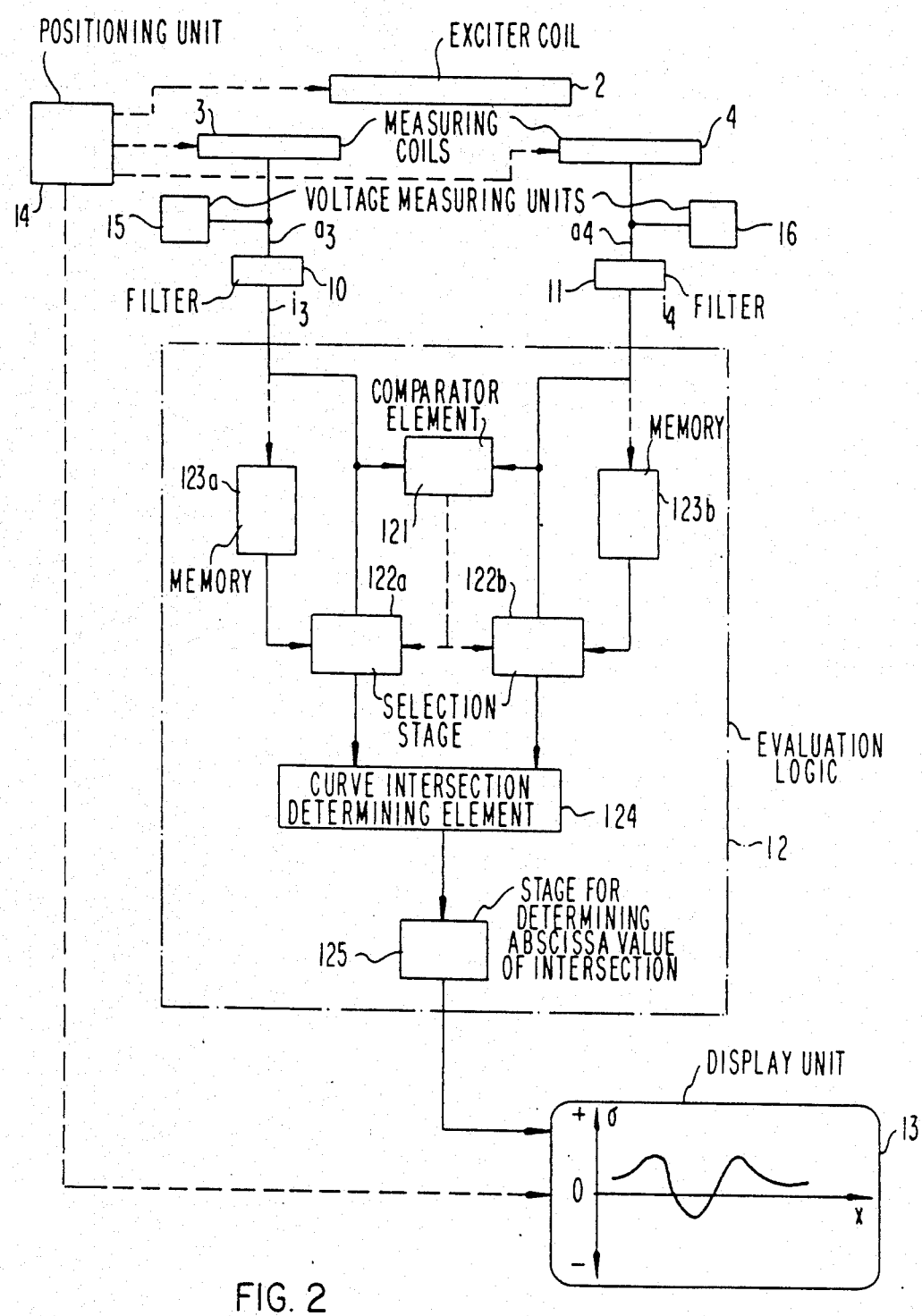
FIG. 2 is a schematic electrical circuit diagram of the apparatus.
Figure 4:
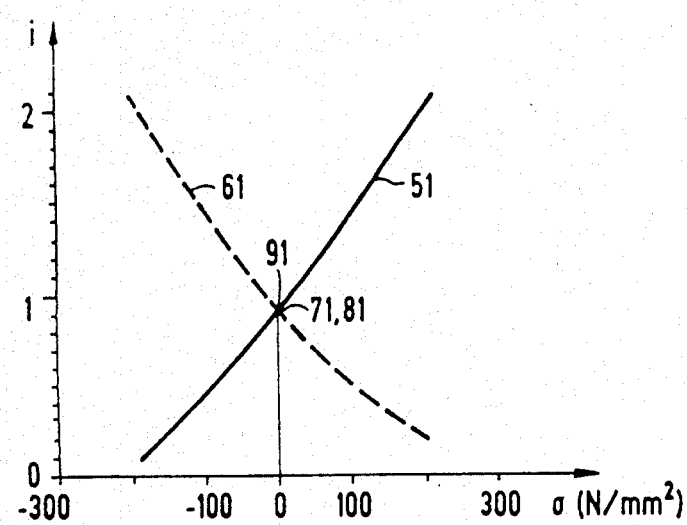
Figure 5:
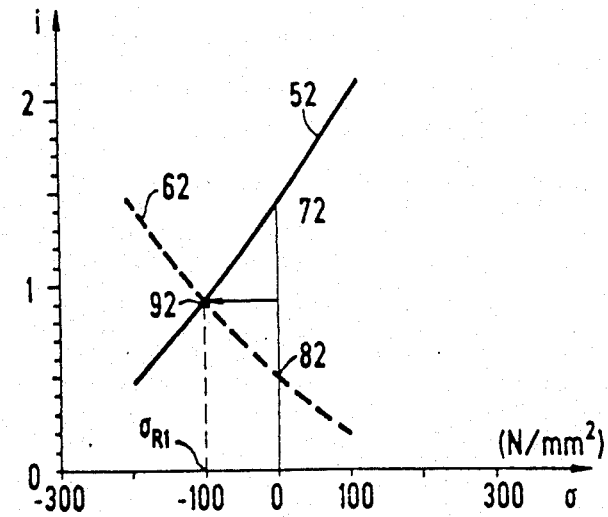

The measuring coils 3 and 4, at which the measuring signals a3 and a4 originate, are each connected through a respective filter 10 and 11, to one evaluation logic 12, as shown in FIG. 2. The filters 10 and 11 only pass the third harmonic component $i_3$ and $i_4$ of magnetic induction. In order to store a family of calibration curves in memory, the output of the filter 10 is connected to a memory 123a, and the filter 11 is connected to a memory 123b. This is represented by dashed lines. In order to measure an internal stress or strain, the filter 10 is connected to a selection stage 122a, to which the memory 123a for calibration curves is also connected, and the filter 11 is connected to a selection stage 122b, to which the memory 123b is also connected. From among calibration curves located in the memories 123a and 123b, those that are to be associated with amplitudes 71 and 81, 72 and 82, 73 and 83 of the third harmonic components $i_3$ and $i_4$ according to FIGS. 4, 5 and 6, are sought in the respective selection stages 122a and 122b. The outputs of the selection stages 122a and 122b are connected to an element 124 for determining the intersection 91, 92, 93 of selective calibration curves 51 and 61, 52 and 62, 53 and 63. In a following association stage 125, the abscissa value of the intersection 91, 92, 93 (FIGS. 4, 5 and 6), which abscissa value stands for the mechanical stress $\sigma_R$, is determined. The output of the association stage 125 forms the output of the evaluation logic 12, which is connected to a display unit 13, for instance a screen. In order to position the measuring coils 3 and 4 relative to the body 1 to be tested, the measuring coils 3 and 4 and the exciter coil 2 are connected to a positioning unit 14. The display unit 13 receives a positioning signal from the positioning unit 14. The internal stresses or strains $\sigma_R(x)$, $\sigma_R(y)$ or $\sigma_R(x, y)$ can be displayed on the display unit 13.

Figure 3:
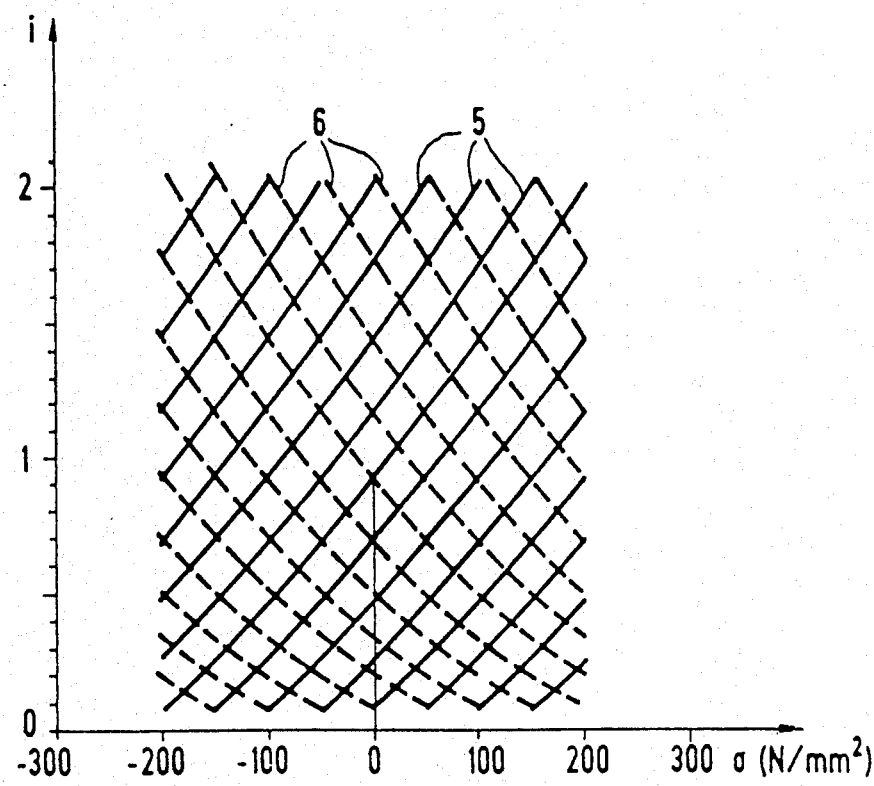

As shown in FIG. 3, families of calibration curves beginning with the numbers 5 and 6 are ascertained for the third harmonic component i of the magnetic induction with the apparatus as described above. The first family beginning with the number 5 indicates the course of the amplitude of the third harmonic component i of the induction in the direction of incident mechanical stresses $\sigma$ and as a function of the magnitude of these stresses $\sigma$. Correspondingly, the second family beginning with the number 6 indicates the course of the amplitude of the third harmonic component i of the magnetic induction vertically of or perpendicular to the incident mechanical stresses $\sigma$ and as a function of the magnitude of these stresses $\sigma$. When the two families beginning with the numbers 5 and 6 are set up, internal stresses are not present in the body 1.

In order to measure unknown mechanical internal stresses $\sigma_R$ in a body 1 which was first subjected to calibration, the amplitudes 71, 72, 73 of the third harmonic component i of the magnetic induction measured in the selected stress direction is determined. as shown in FIGS. 4, 5 and 6. In addition, the amplitude 81, 82, 83 of the third harmonic component i of the magnetic induction vertically or perpendicularly thereto is determined.

Both amplitude values 71, 72, 73 and 81, 82, 83 are plotted on the ordinate of the coordinate system ($\sigma$, i) at $\sigma=0$. One calibration curve 51, 52, 53 from the first family beginning with the number 5 is defined by the value 71, 72, 73, and one calibration curve 61, 62, 63 from the second family beginning with the number 6 is defined by the value 81, 82, 83. The abscissa value of the intersection point 91, 92, 93 of the two curves 51, 52, 53 and 61, 62, 63 indicates the magnitude of the internal mechanical stress $\sigma_R$.

If, as in FIG. 4, the amplitudes 71 and 82 are of equal magnitude, then the calibration curves 51 and 61 intersect at the intersection point 91 at $\sigma=0$. Therefore an internal stress is not present ($\sigma_R=0$).

If, as in FIG. 5, the amplitude 72 in the selected stress direction is greater than the amplitude 82 at right angles to the selected stress direction, the calibration curves 52 and 62 intersect in the first quadrant of the coordinate system at the intersection point 92. Therefore a tensile internal stress $\sigma_{R1}$ is present, the quantity of which is defined by the abscissa value of the intersection point 92.

If, as in FIG. 6, the amplitude 73 in the selected stress direction is lower than the amplitude 83 vertically or perpendicularly thereto, the calibration curves 53 and 63 intersect in the fourth quadrant of the coordinate system at the intersection point 93. Therefore a compressive internal stress $\sigma_{R2}$ is present, the quantity of which is defined by the abscissa value of the intersection point 93.

The values $\sigma_{R1}$, $\sigma_{R2}$ quantitatively describe the magnitude of the internal stress at the selected measurement site $x=0$, $y=0$ of the body 1.

With this method, stresses $\sigma$ can be measured in principle in any arbitrary direction $\sigma$. One advantage is as follows:

By rotating the coils 3, 4 in the direction of the double arrow P, until the electrical measurement voltage at one of the coils 3, 4 has attained a maximum, the primary mechanical stresses can be measured. In FIG. 1, these are in the x' and y' direction, for example.

In order to detect the maximum measuring voltage, each coil 3, 4 as shown in FIG. 2 is connected to a voltage measuring unit 15, 16, which has means for displaying the voltage measured.

In order to ascertain only qualitatively whether internal tensile stress or internal compressive stress is present, it is sufficient to use a comparator element 121 connected to the output side of the filters 10 and 11 in FIG. 2. In this element it is ascertained which of the values i₃ and i₄ is greater, or whether the two values are equal. The result is displayed by means of a display element present in a comparator element 121. However, it may also be supplied as additional information to the selection stages 122a and 122b through connecting lines represented by dashed lines in FIG. 2.

I claim:

1. Method for measuring the mechanical internal stress of a body of ferromagnetic material, which comprises:
    (a) generating a sinusoidal magnetic field at given site of a ferromagnetic body and developing an induction with a third harmonic component;
    (b) measuring first and second amplitudes of the third harmonic component of the induction at first and second measuring sites at the body being mutually spaced apart by an angle of 90° with respect to the given site;
    (c) locating an associated first curve from a first predetermined family of curves representing the third harmonic component of the induction as a function of the mechanical stress for the first amplitude, and locating an associated second curve from a second predetermined family of curves representing the third harmonic component of the induction as a function of the mechanical stress for the second amplitude;
    (d) determining a point of intersection of the first and the second curves; and
    (e) defining a given direction by a connecting line passing through the given site of the sinusoidal magnetic field and through the first measuring site, and determining the abscissa value of the point of intersection beginning at a predetermined abscissa value as a measured value for the magnitude of the mechanical internal stress in the given direction.

2. Method according to claim 1, which comprises associating the first family of curves with a first predetermined measuring direction and associating the second family of curves with a second measuring direction perpendicular to the first predetermined measuring direction.

3. Method according to claim 1, which comprises associating the first family of curves with a direction parallel to a first predetermined measuring direction and associating the second family of curves with a second measuring direction perpendicular to the first predetermined measuring direction.

4. Method according to claim 1, which comprises determining the direction of the mechanical internal stress by varying the first and second measuring sites relative to the given site of the sinusoidal magnetic field while maintaining the angular spacing of 90°, until a maximum amount of the third harmonic component of the magnetic induction is measured at one of the first and second measuring sites, and recording the direction determined by the given site of the sinusoidal magnetic field and the measuring site of the maximum amount of the third harmonic component of the magnetic induction, as the direction of the internal mechanical stress.

5. Method according to claim 4, which comprises generating the sinusoidal magnetic field with an exciter coil.

6. Method according to claim 1, which comprises determining the magnetic induction by measuring the induction voltage in measuring coils.

* * * * *